United States Patent [19]

Borrebaeck et al.

[11] Patent Number: 5,712,089
[45] Date of Patent: Jan. 27, 1998

[54] METHOD OF SELECTING SPECIFIC BACTERIOPHAGES

[75] Inventors: Carl A. K. Borrebaeck, Hjärup, Sweden; Marta Duenas, Ciudad Habana, Cuba

[73] Assignee: Bioinvent International AB, Lund, Sweden

[21] Appl. No.: 640,792

[22] PCT Filed: Dec. 5, 1994

[86] PCT No.: PCT/SE94/01166

§ 371 Date: Oct. 7, 1996

§ 102(e) Date: Oct. 7, 1996

[87] PCT Pub. No.: WO95/16027

PCT Pub. Date: Jun. 15, 1995

[30] Foreign Application Priority Data

Dec. 6, 1993 [SE] Sweden .................................. 9304060

[51] Int. Cl.$^6$ .................. C12Q 1/07; C12Q 1/02; G01N 33/53; C12P 21/04
[52] U.S. Cl. .................. 435/5; 435/7.1; 435/69.3; 435/69.6; 435/172.3; 435/69.7; 435/252.3; 435/252.33
[58] Field of Search .................. 435/7.1, 5, 7.2, 435/69.6, 69.9, 69.3, 252.3, 252.33, 69.7, 6, 172.3; 530/412, 387.1

[56] References Cited

FOREIGN PATENT DOCUMENTS 9301288  1/1993  WIPO .................. C12N 15/13

OTHER PUBLICATIONS

McCafferty et al., 1990, Nature, vol. 348; pp. 552–554.
Methods In Enzymology, vol. 217, 1993, G.P. Smith, et al "Libraries of Peptides and Proteins Displayed on Filamantous Phage" pp. 228–257.
Nucleic Acis Research, vol. 21, No. 9, 1993, P. Waterhouse, et al, "Combinatorial infection and in vivo recombination, a stragegy for making large phage antibody repertoires" pp. 2265–2266.
Proc. Natl. Acad. Sci., vol. 87, Apr. 1990, D.M. Kurnit, et al, "Improved genetic selection for screening bacteriophage libraries by homologous recombination in vivo" pp. 3166–3169.
Gene, vol. 109, 1991, W. Markland, et al, "Design, construction and function of a multicopy display vector using fusions to the major coat protein of bacteriophage M13" pp. 13–19.
Bio/Technology, vol. 12, Oct. 1994, M. Duenas et al., "Clonal Selection and Amplication of Phage Displayed Antibodies by Linking Antigen Recognition and Phage Replication" pp. 999–1002.

*Primary Examiner*—Mary E. Mosher
*Assistant Examiner*—Ali R. Salimi
*Attorney, Agent, or Firm*—Larson & Taylor

[57] ABSTRACT

A method for selecting a molecule such as an antibody, antigen, peptide, protein or fragment thereof, which molecule is expressed together with a phage coat protein on the phage's surface. The method is characterised by linking phage replication to recognition of the molecule on the surface of the phage. The linkage can be achieved by use of a fusion protein between phage protein 3 and a specific binding ligand for the molecule.

8 Claims, 2 Drawing Sheets

METHOD OF SELECTING SPECIFIC BACTERIOPHAGES

TECHNICAL AREA OF THE INVENTION

The present invention concerns a method for selecting a molecule, such as an antibody, antigen, peptide, protein or fragment thereof, which molecule is expressed together with a phage coat protein on the phage's surface.

BACKGROUND OF THE INVENTION

Monoclonal antibodies were introduced in 1975 by George Köhler and Cesar Milstein. The concept comprises fusing immune B lymphocytes from mice with a tumour cell line, for instance a myeloma/plasmacytoma. The resulting hybrid myeloma (=hybridoma) will posses the following two distinct properties: 1. produce specific antibodies; and 2. live infinitely in cell culture. The first of these properties is inherited from the immune mouse cells, whereas the second one comes from the tumour cell line. The hybridoma prepared as outlined above, will produce so-called monoclonal antibodies of high specificity and in infinite amounts; properties which makes them especially suitable for use in biomedical applications.

Human therapy using monoclonal antibodies does however require human antibodies, among other because an unwanted glycosylation appears on the mouse antibodies, which renders these antibodies directly unsuitable for human therapy (Borrebaeck et al., 1993). Human monoclonal antibodies have however shown themselves to be considerably much harder to produce than the mouse antibodies, especially because human beings can not be immunised due to ethical considerations. This means that the starting material, i.e. the immune B lymphocytes, has not been optimal. The main problem has been that the number of immune B lymphocytes has been very low in non-immunised individuals, which makes it extremely difficult to select specific antibodies from said B lymphocytes.

In 1985 Smith (Smith, 1985) published a method which dramatically changed how antibodies and especially human antibodies could be produced. Smith showed how small peptides could be expressed together with a phage coat protein on a filamentous phage (virus which infects bacteria). As filamentous phages allow even foreign proteins to be expressed on some of their own coat proteins, such as for instance protein 3 or protein 8, these phages are very well suited for expression of even the relatively big antibody fragments, such as for instance Fab of Fv (McCaffery et al., 1990; Barbas et al., 1991; Huse 1991).

The method for placing the antibody fragment on the phage surface is the following:

From a starting material which comprises B lymphocytes, such as blood, lymphoid tissue or the like, the B lymphocytes are separated and a gene library of the antibodies produced by said B lymphocytes is erected. The genes encoding the variable heavy and light antibody domains ($V_H$ and $V_L$) are amplified through the so-called PCR-method (PCR=Polymerase Chain Reaction), which was first described applied on antibodies by Larrick et al. (1989). These amplified gene segments, which codes for all different antibody specificities found in the starting material used, are thereafter cloned into a so-called phagemid vector with a random combination of different $V_H/V_L$ genes (Huse et al., 1989). The result of this cloning is that all available specificities can be immortalised in one single step and in a following step they may be expressed on the surface of a filamentous phage together with for example coat protein 3. Those phages which express an antibody fragment with the sought after specificity can then be selected by taking advantage of the surface displayed antigen receptor, i.e. the antibody fragment. In summary, it can be said that all antibody specificities in a certain starting material can be directly immortalised by PCR amplification and thereafter expressed on the surface of a phage.

Theoretically this method gives access to the complete pool of antibodies found in the immune system. This pool consists of up to $10^{14}$ different antibody specificities and at a given point of time in a human beings life approximately $10^8$–$10^9$ different specificities will be available. The selection of one (1) antibody specificity out of the pool of for instance $10^9$ is a very difficult task, in many cases impossible if there are not more than one or a few copies of the wanted specificity.

Different modes of selection have been published, all of which depend on for instance conventional affinity chromatography of the phages or simply a panning procedure where the phages are bound to an antigen covered plastic surface from which the specifically bound phages, i.e. those containing a specific antibody fragment can be isolated. Antigen specific panning and affinity chromatography will in the best of cases only reward a purification factor of 1000 times, and in many cases only a factor of 50–100 times per step.

DEFINITION OF THE INVENTION

It has now been found that a surprisingly much simpler and more efficient selection of the phages expressing antibodies or antibody fragments of wanted specificity on their surface can be achieved by linking specific phage replication to the antigen recognition of said antibodies or antibody fragments on the phage's surface.

Further, the selection according to this invention, although especially suitable for selecting human antibodies, may be used for the selection of any molecule, which may be expressed on the surface of a phage together with phage coat protein3.

Examples of such molecules are peptides, proteines, antigens, antibodies and fragments thereof, and in this specification and the claims, the term "ligand I" will be used to denominate said molecules.

Further, the term "ligand II" will, in this specification and the claims, be used to denominate any group or molecule, which can interact specifically, i.e.bind or be bound by said ligand I on the surface of a phage. Examples of groups or molecules which may act as ligand II are peptides, proteins or fragments thereof, organic molecules, hormones or fragments thereof.

DETAILED DESCRIPTION OF THE INVENTION

The aim of the method according to the present invention is to make available an efficient method of selection based on that specific recognition of a phage, through a ligand I on its surface leads to an ability to replicate and multiply.

The present invention links recognition of a ligand carried on the phage and the phage's replication. This a direct mimicry of the humoral immune system theory of clone selection where only antigen specific B lymphocytes proliferate and differentiate in an antigen driven process. Since ligand recognition is linked to phage replication this means that only the specific phages replicate, i.e. multiply and this makes possible an easy selection of the phage carrying a ligand even if this phage is surrounded by hundred thousands of non-specific phages.

The method according to the present invention which comprises linking specific phage replication and recognition of a ligand I on the phage surface, is achieved by a.) letting a helper phage stock, which phages do not have gene3 but carry protein3 in their coats, infect bacteria which carry a phagemid vector with a cloned ligand I;

b.) add a fusion protein comprising protein3 or a part thereof, and a ligand II specifically interacting with said ligand I, so that ligand I and ligand II bind specifically to each other;

c.) let said specific phages, which carry ligand I, ligand II and protein3 on their surface infect bacteria and thereby replicate and multiply.

Any filamentous phage may be used as helper phage by removal of gene3, because this renders the phage non-infectious since protein3, expressed by gene3, is the protein which binds to the pili of the bacterium and thereby mediates an infection of bacteria by phages. Examples of filamentous phages, which may be transformed into helper phages usable in this invention are M13, fd and fl. It is preferred to use a M13 helper phage, which after the removal of gene3 has been named M13 MDΔ3.

The fusion protein may be a true fusion protein or a similarly linked molecule making available a combination of protein3 and a ligand II. In this specification and the claims, the term "fusion protein" is used in the meaning to encompass both genetically produced fusion proteins and chemically linked molecules of protein3 and ligand II, and further, the term "fusion protein" is also ment to encompass molecular structures constructed with a receptor-ligand pair between protein3 and ligand II. An example of such a receptor-ligand pair is biotin-avidin, but other such receptor-ligand pairs are well-known in the art. Thus, the "fusion protein" may be any combination linking protein3 and ligand II, directly or indirectly.

The ligand II in the fusion protein, for instance an antigen, will interact specifically with those phages having a specific ligand I, an antibody or antibody fragment, on their surface and these phages can now infect bacteria, such as $E.$ $coli,$ as ligand II is linked to protein3, which mediates infection. Thereby, replication and multiplication can occur and the ligand recognition is linked to specific phage replication. All other phages which are non-specific for the ligand II in the fusion protein do not receive the ability to infect are left behind as a background during the selection process.

In order to produce a helper phage stock of a truncated infectious phage, such as for instance M13MDΔ3, this is transfected into bacteria, such as $E$ $coli,$ which already contain gene3 on a plasmid, for example a pUC19 plasmid. The resulting extruded phage, will not contain gene3 but protein3 and can thus only infect bacteria, such as $E.$ $coli$ once. The thus produced helper phage stock is now used to infect $E.$ $coli$ containing phagemid vectors with cloned regions from different ligands, for example antibodies. The result will be a new phage stock where the phages express a ligand I on their surface linked to a truncated protein3 from the phagemid vector. These phages cannot infect again and thus they can not replicate and multiply.

Apart from the plasmid pUC19, any other bacterial expression vector may be used for cloning gene3 into the bacteria.

The method according to the invention, linking replication of a phage to specific recognition, allows for the first time the use of starting materials for generation of antibodies, which includes only very few copies, because it makes possible the amplification of the specific phage many million times. In this manner a method is created which gives access to the wanted antibody specificities after the same principle which the body uses for selecting its antibody specific B cells.

It is especially preferred to use the process according to the present invention for selection of human antibodies, by using said human antibody as ligand I.

WORKING EXAMPLES

Preparation of Helper Phage Stock, M13MDΔ3

The construction of a mutant phage M13MDΔ3 (devoid of gene 3) was performed by digestion of the replicative form (RF) DNA of M13KO7 (Viera, J. and Messing, J. 1987) with BspHI and Xmnl removing the fragment between residue 1299 and 2646 (according to the numbering of Wezenbeek et al. (Wezenbeek, P. M. G. F., Huselbos, T. J. M. and Schoenmarkers, G. G. 1980) In order to reincorporate a fragment from residue 1299 to 1525 containing gene VIII and part of gene IX, this sequence was PCR amplified from M13 KO7 template using the primers 1299 (BspHI): 5'-ACTTCCTCATGAAAAAGTC-3' and 1525 (Xmnl): 5'-GGGAAATTATTCTTATCAGCTTGC-3'. Following digestion, the PCR fragment was cloned in the 7.3 kb RF DNA originating from M13KO7. Helper phage stocks were prepared as described (Hoogenboom, H. R., Griffiths, A. D., Johnson, K. S., Chiswell, D. J., Hudson, P. and Winter, G. 1991), except for the use of TG1 transformed with pUC19 vector, containing gene 3 that produced an intact protein 3 from M13. The result phage thus had the same proteins as the wild type but did not contain gene 3. This phage was able to infect a male host cell once but any subsequently extruded particles were non-infectious.

EXAMPLE 1

Figure 1:
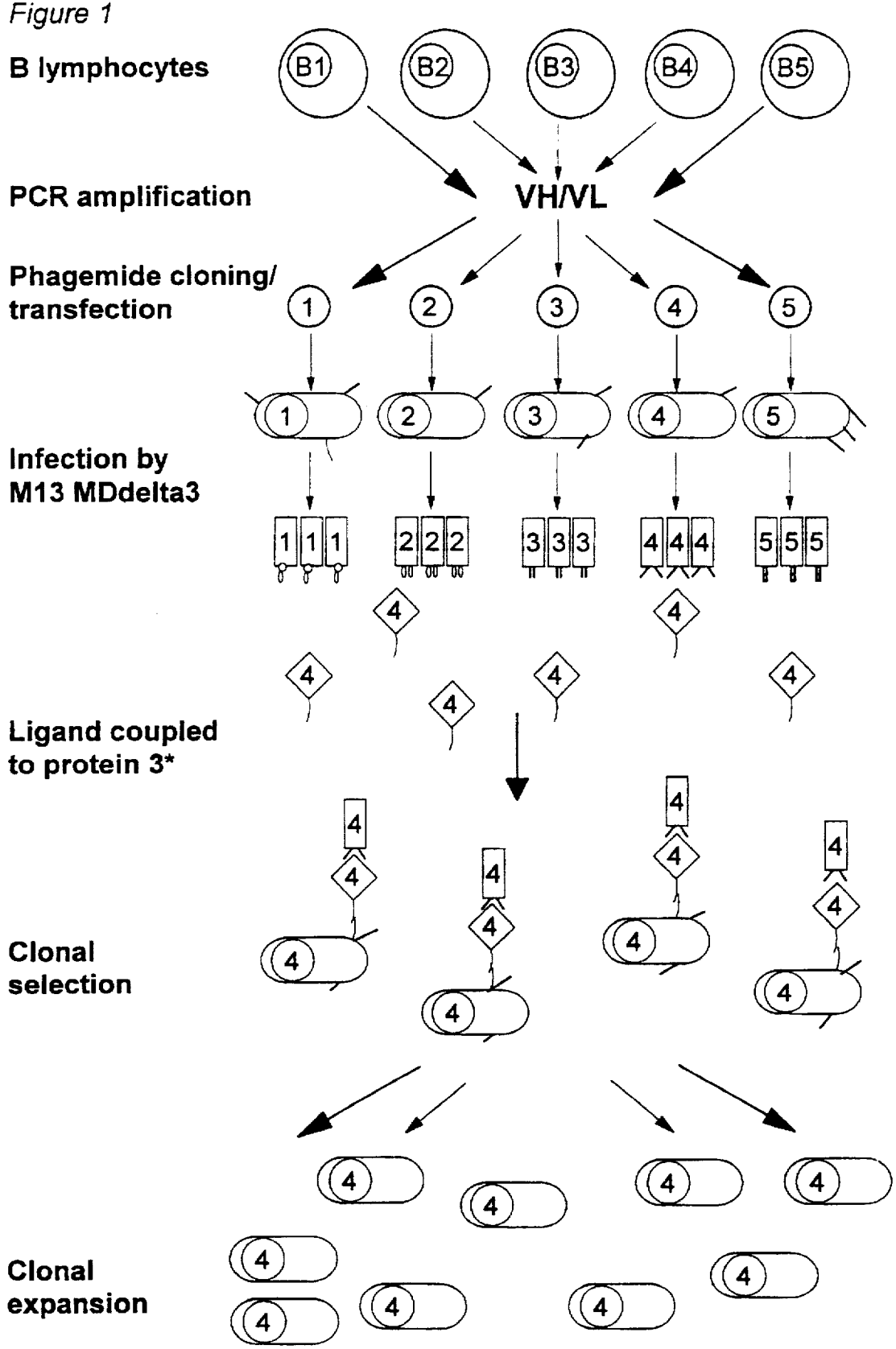
FIG. 1 gives a description of the principle for linking ligand recognition to phage replication by selection of specific phages according to the present invention (* M13 MDdelta3 is a helper phage lacking gene 3, i.e. not itself infectious).
Figure 2:
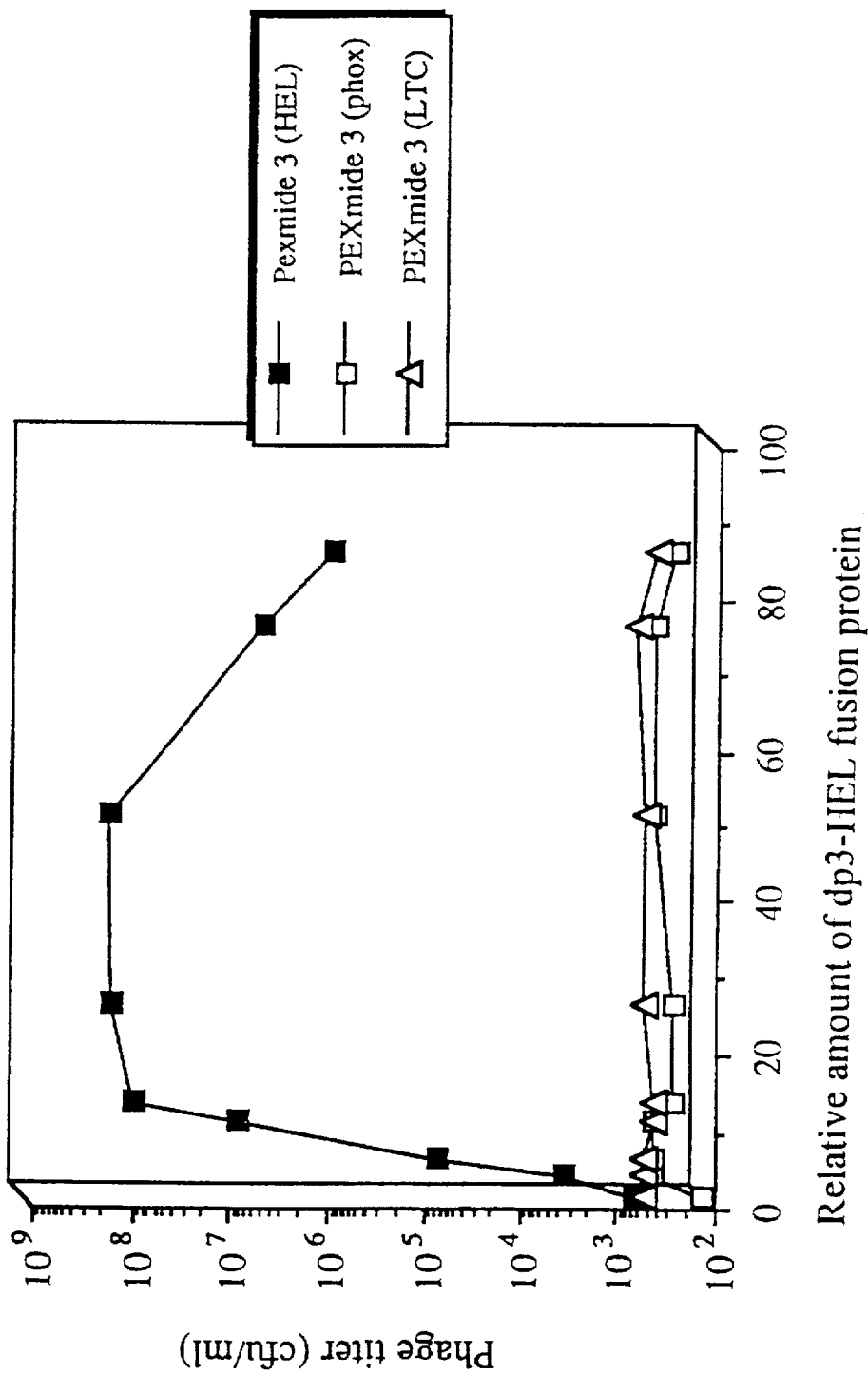
FIG. 2 shows the result of an experiment where the specificity and selectivity of the selection process is demonstrated.

Three different phage stocks, where each stock contain phages which express antibody fragments specific for respectively hen egg lysozyme (HEL), phenyloxazolon (phox) or gp120 on the human immunodeficiency virus (LTC), were prepared separately. The three different phagemids are transfected into XL1 Blue bacteria and are cultivated with ampicillin selection. Thereafter these bacteria are infected with a helper phage, M13MDΔ3, which does not itself contain gene3, thereby producing non-infectious phage stocks since protein 3 which mediates infection is not included. The three different phage are prepared by centrifugation and filtration and are mixed with different amounts of a fusion protein between a truncated protein3 (only the 98 N-terminal amino acids) and HEL (dp3-HEL), whereupon it is incubated over night. The following day XL1 Blue bacteria are infected with these three phage stocks and FIG. 2 shows that only the phages carrying the correct receptor on their surface, i.e. the antibody fragment specific for HEL has been given the ability to replicate and multiply. The linking between ligand recognition and replication has increased the specific phage titre from a background level of $10^2$ up to more than $10^8$ cfu/ml, which is a specific increase of more than a million times. Further, (as appears from the FIG. 2), the non specific phages did not replicate at all, but stayed on the background titre of $10^2$ cfu/ml.

EXAMPLE 2

Three different phagemids, which express antibody fragments specific for hen egg lysozyme (HEL) or phenyloxazolon (phox) or gp120 on the human immunodeficiency virus (LTC), were mixed in the relation 1:1500:1500. This mixture were transfected into XL1 Blue bacteria and are cultivated with ampicillin selection. Thereafter these bacteria are infected with a helper phage, M13MDΔ3, which does not itself contain gene3, thereby producing non-infectious phages. The phages are prepared by centrifugation and filtration and are mixed with 30 weight % of a fusion protein of a truncated protein3 ( only the 98 N-terminal amino acids) and HEL (dp3-HEL), which is incubated over night. The following day XL1 Blue indicator bacteria are infected with this phage stock and are cultivated over night with ampicillin selection. A little more than one hundred colonies are selected and are cultivated further in a 96 hole cultivating plate where they are infected by the wild type of the helper phage M13KO7, which carries the gene3. This results in the production of phages from every colony, which can be detected using a phage-ELISA. Table 1 shows that the concentration factor in the first antigen specific step is >$10^5$ times and approximately $10^{10}$ times after the second selection step. This happens because the fusion protein (dp3-HEL) links antigen recognition with specific replication of HEL specific phages, i.e. phages expressing the antibody fragment specific against HEL on their surface.

REFERENCES

Barbas, C. F., Kang, A. S., Lerner, R. A. & Benkovic, S. J. *Proc. Natl. Acad. Sci.* (USA) 88, 7978 (1991).

Borrebaeck, C. A. K., Malmborg, A. & Ohlin, M. *Immunol. Today* 14, 477 (1993).

Huse, W. D., Sastry, L., Iverson, S. A., Kang, S. A., Alting, M. M., Burton, D. R., Benkovic, S. J. & Lerner, R. A. *Science* 246, 1275 (1989).

Huse, W. D. In *Antibody Engineering; A Practical Approach* (Borrebaeck, C. A. K., ed.) p. 103, W. H. Freeman and Co., New York (1991).

Larrick, J. W., Danielsson, L., Brenner, C. A., Abrahamsson, M., Fry, K. E. & Borrebaeck, C. A. K. *Biochem. Biophys. Res. Commun.* 160,1250 (1989).

McCafferty, J., Griffiths, A. D., Winter, G. & Chiswell, D. J. *Nature* 348, 552 (1990).

Smith, G. P. *Science* 228, 1315 (1985).

Viera, J. and Messing, J. 1987. Production of single strand plasmid DNA. 1987. *Meth. Enzymol.* 153:3–11

Wezenbeek, P. M. G. F., Huselbos, T. J. M. and Schoenmarkers, G. G. 1980. Nucleotide sequence of filamentous bacteriophage M13 DNA genome: comparison with phage fd. *Gene* 11:129–148.

Hoogenboom, H. R., Griffiths, A. D., Johnson, K. S., Chiswell, D. J., Hudson, P. and Winter, G. 1991. Multisubunit proteins on the surface of filamentous phage: Methodologies for displaying antibody (Fab) heavy and light chains. *Nucleic Acid. Res.* 19:4133–4137.

TABLE 1

| Clonal mixture | Initial ratio | Final ratio | Enrichment factor |
|---|---|---|---|
| First round of enrichment | | | |
| pEXmide HEL/ pEXmide Phox + pEXmide LTC | | | |
| | 1/3 × $10^4$ | 82/20 | 1.2 × $10^5$ |
| | 1/3 × $10^5$ | 49/59 | 2.5 × $10^5$ |
| | 1/3 × $10^6$ | 4/104 | 1.1 × $10^5$ |
| | 1/3 × $10^7$ | 0/108 | — |
| Second round of enrichment | | | |
| | 1/3 × $10^8$ | 103/5 | 6.1 × $10^9$ |
| | 1/3 × $10^9$ | 55/53 | 3.1 × $10^9$ |
| | 1/3 × $10^{10}$ | 16/92 | 5.2 × $10^9$ |
| | 1/3 × $10^{11}$ | 2/106 | 5.6 × $10^9$ |
| | 1/3 × $10^{12}$ | 0/108 | |

We claim:

1. A method of enrichment for filamentous bacteriophages presenting specific ligand I on the phage surface, comprising the steps of:
   a) transfecting bacteria with a phagemid expressing ligand I;
   b) infecting said transfected bacteria with a helper filamentous phage containing wild-type protein 3 but lacking gene 3, so that the bacteria produce non-infectious phages which lack protein 3 and which present ligand I on the surface;
   c) adding to said non-infectious phages a protein 3/ligand II fusion protein, wherein the protein 3/ligand II fusion protein specifically binds to ligand I on the surface of said non-infectious phages, producing phages able to infect bacteria; and
   d) infecting bacteria with the resulting phages, so that those phages presenting ligand I are selected and clonally expanded by replication and multiplication by said bacteria.

2. The method of claim 1, wherein ligand I is an antibody or antibody fragment, and ligand II is an antigen.

3. The method of claim 2, wherein the antibody or antibody fragment is human.

4. The method of claim 1, wherein the protein 3/ligand II fusion protein comprises all of the protein 3 sequence.

5. The method of claim 1, wherein the protein 3/ligand II fusion protein comprises part of the protein 3 sequence.

6. The method of claim 1, wherein the non-infectious phages which lack protein 3 and which present ligand I on the surface, produced in step (b), are present in a mixture comprising phages which lack protein 3 and which do not present ligand I on the surface.

7. The method of claim 6, wherein the phages which present ligand I and phages which do not present ligand I are present in a ratio ranging from 1:3×$10^4$ to 1:3×$10^{11}$.

8. The method of claim 1, further comprising a step wherein the infected bacteria of step (d) are further infected with a helper phage, thereby replicating and multiplying ligand I presenting phages.

* * * * *